United States Patent [19]

Van Ness et al.

[11] Patent Number: 5,124,444
[45] Date of Patent: Jun. 23, 1992

[54] LACTAM-CONTAINING COMPOSITIONS AND METHODS USEFUL FOR THE EXTRACTION OF NUCLEIC ACIDS

[75] Inventors: Jeffrey Van Ness, Bothell; Nicolaas Vermuelen, Woodinville; B. Melina Cimler, Bothell, all of Wash.

[73] Assignee: MicroProbe Corporation, Bothell, Wash.

[21] Appl. No.: 384,367

[22] Filed: Jul. 24, 1989

[51] Int. Cl.$^5$ .................. C12Q 1/68; G01N 1/18
[52] U.S. Cl. .......................... 536/27; 435/6; 540/451; 540/463; 540/485; 540/526; 546/243; 548/543; 548/546; 548/547; 436/178
[58] Field of Search .............. 548/543, 546, 547; 546/243; 540/451, 463, 485, 526, 527; 536/27; 435/6; 436/178

[56] References Cited

U.S. PATENT DOCUMENTS 4,483,920  11/1984  Gillespie et al.

FOREIGN PATENT DOCUMENTS 0127327  4/1984  European Pat. Off.
87/1023  11/1987  PCT Int'l Appl.

OTHER PUBLICATIONS

Marmur, *J. Mol. Biol.* 3:208–218 (1961).
Chirgwin et al., *Biochem.* 18:5294–5299 (1979).
Dunn and Hassell, *Cell* 12:23–36 (1977).
Thompson and Gillespie, *Anal. Biochem.* 163:281–291 (1987).
Bresser et al., *DNA* 2:243–254 (1983).
Manser and Gefter, *Proc. Natl. Acad. Sci. USA* 81:2470–2474 (1984).

*Primary Examiner*—Robert A. Wax
*Assistant Examiner*—F. Tsung
*Attorney, Agent, or Firm*—Debra K. Leith

[57] ABSTRACT

This invention relates to novel methods for the extraction of nucleic acid. In particular methods are described for isolating nucleic acid from a sample containing a complex biological mixture of nucleic acid and non-nucleic acids wherein the sample is combined with an extraction solution comprising a lactam and then the nucleic acid material is isolated from the resulting combined solution. The resulting combined solution is mixed and becomes biphasic and the nucleic acid material is isolated from the aqueous phase by precipitation with ethanol. The lactam is preferably about 5 to about 70% of the extraction solution and is most preferably 2-pyrrolidone, N-ethyl-2-pyrrolidone, N-cyclohexyl-2-pyrrolidone, N-dodecyl-2-pyrrolidone, N-methyl-2-pyrrolidone, N-hydroxyethyl-2-pyrrolidone, N-methyl-2-piperidone, 2-ε-caprolactam, N-methyl-2-caprolactam, 2-piperidone or N-(4-hydroxybenzyl)pyrrolidone. Methods for selectively isolating DNA, ribosomal RNA and plasmid DNA are also disclosed.

19 Claims, 2 Drawing Sheets

METHOD A:
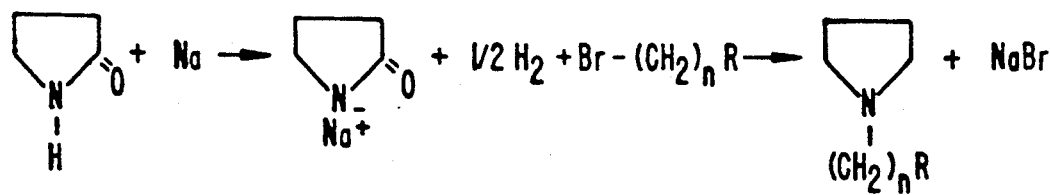
FIG. $IA_1$
METHOD B:
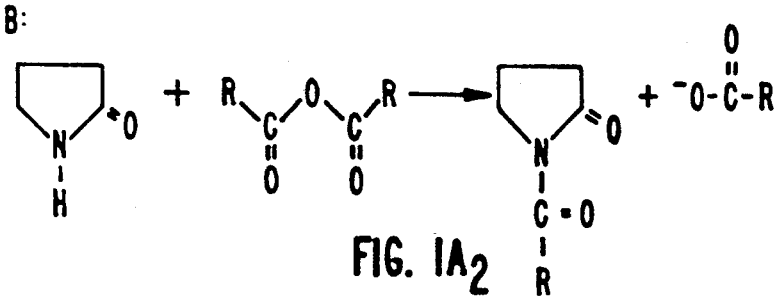
FIG. $IA_2$
METHOD C:
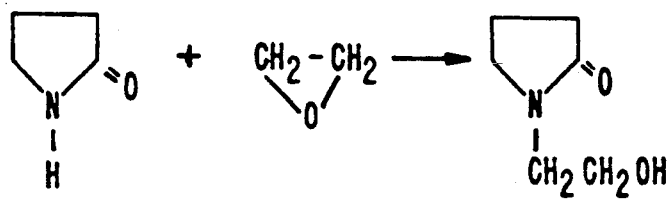
FIG. $IA_3$
METHOD D:
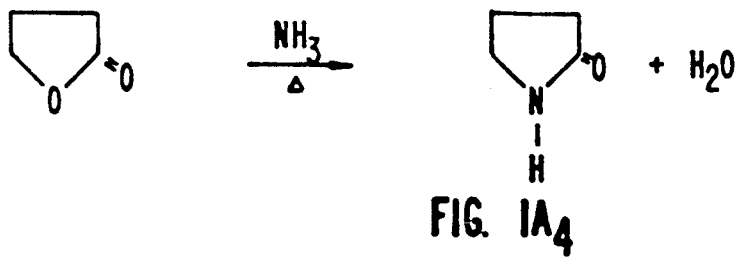
FIG. $IA_4$
METHOD E:
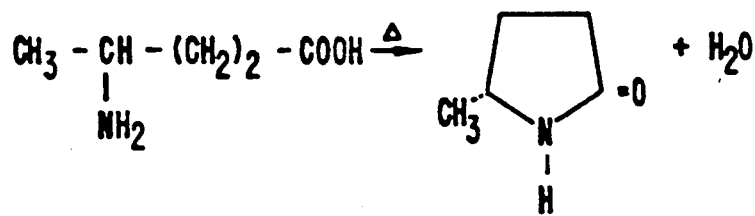
FIG. $IA_5$ METHOD F:
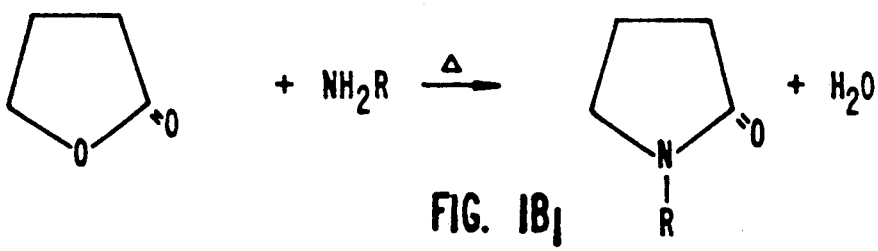
FIG. 1B₁
METHOD G:
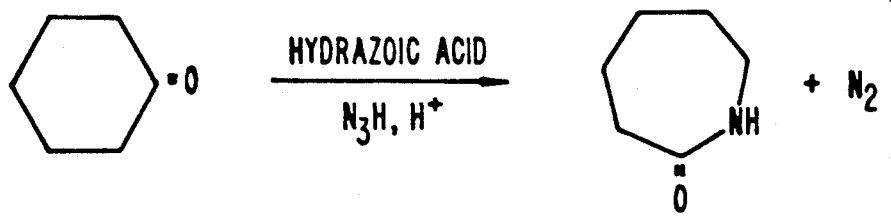
WHERE 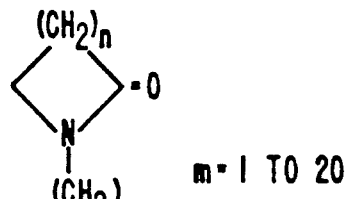 IS PREPARED BY METHODS A, D
$m = 1$ TO $20$
WHERE 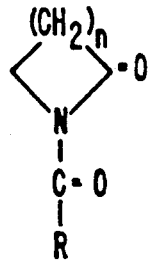 IS PREPARED BY METHOD B
WHERE 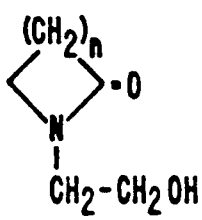 IS PREPARED BY METHOD C
WHERE IS PREPARED AS DESCRIBED:
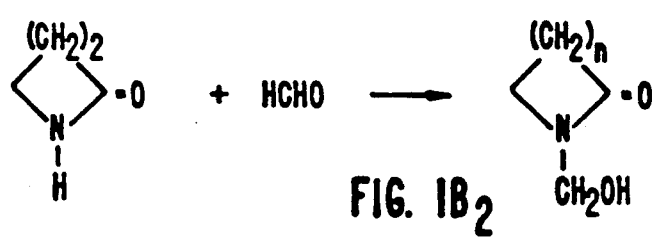
FIG. 1B₂

“5,124,444”

LACTAM-CONTAINING COMPOSITIONS AND METHODS USEFUL FOR THE EXTRACTION OF NUCLEIC ACIDS

BACKGROUND OF THE INVENTION

1. Field of the Invention

This invention relates to compositions and assay methods for the extraction and hybridization of nucleic acids. In particular this invention relates to compositions and methods to extract nucleic acids from cells in complex biological samples or specimens. The method is based on the use of the chemical family of compounds termed lactams, preferably pyrrolidones, which promote nucleic acid base pairing and which are effective in the extraction and purification of nucleic acids.

2. Brief Description of the Relevant Art

Organic solvents such as phenol and chloroform are traditionally used in techniques employed to isolate nucleic acid from procaryotic and eucaryotic cells or from complex biological samples. Nucleic acid isolations typically begin with an enzymatic digest performed with proteases followed by cell lysis using ionic detergents and then extraction with phenol or a phenol/chloroform combination. The organic and aqueous phases are separated and nucleic acid which has partitioned into the aqueous phase is recovered by precipitation with alcohol. However, phenol or a phenol/chloroform mixture is corrosive to human skin and is considered as hazardous waste which must be carefully handled and properly discarded. Further, the extraction method is time consuming and laborious. Marmur, *J. Mol. Biol.*, 208-218 (1961), describes the standard preparative procedure for extraction and purification of intact high molecular weight DNA from procaryotic organisms using enzymatic treatment, addition of a detergent, and the use of an organic solvent such as phenol or phenol/chloroform. Chirgwin et al., *Biochemistry* 18:5294-5299 (1979) described the isolation of intact RNA from tissues enriched in ribonuclease by homogenization in guanidine thiocyanate and 2-mercaptoethanol followed by ethanol precipitation or by sedimentation through cesium chloride.

Further, the use of chaotropic agents such as guanidine thiocyanate (GnSCN) are widely used to lyse and release nucleic acid from cells into solution, largely due to the fact that the chaotropic salts inhibit nucleases and proteases. However, it has proved difficult to isolate the nucleic acids from these chaotropic salt solutions due to the incompatibility of the chaotropes with ionic detergents and the inability to easily partition the nucleic acid into an aqueous phase given such high molar concentrations of salt used and the chaotropic behavior of the salts.

Nucleic acid hybridization is a known and documented method for identifying nucleic acids. Hybridization is based on base pairing of complementary nucleic acid strands. When single stranded nucleic acids are incubated in appropriate buffer solutions, complementary base sequences pair to form double stranded stable molecules. The presence or absence of such pairing may be detected by several different methods well known in the art.

Most hybridization assays previously described involve multiple steps such as the hybridization technique described by Dunn & Hassell in Cell, Vol. 12, pages 23-36 (1977). Their assay is of the sandwich-type whereby a first hybridization occurs between a "target" nucleic acid and a "capture" nucleic acid probe which has been immobilized on a solid support. A second hybridization then follows where a "signal" nucleic acid probe, typically labelled with a radioactive isotope hybridizes to a different region of the immobilized target nucleic acid. The hybridization of the signal probe may then be detected by, for example, autoradiography.

SUMMARY OF THE INVENTION

This invention relates to novel methods for the extraction and hybridization of nucleic acids. In particular, methods are described for isolating nucleic acid from a sample containing a complex biological mixture of nucleic acid and non-nucleic acids wherein the sample is combined with an extraction solution comprising a lactam and then the nucleic acid material is isolated from the resulting combined solution. The resulting combined solution is further mixed and allowed to become biphasic and the nucleic acid material is isolated from the aqueous phase. The lactam is preferably about 5 to about 70% of the extraction solution, and is most preferably 2-pyrrolidone, N-ethyl-2-pyrrolidone N-cyclohexyl-2-pyrrolidone, N-dodecyl-2-pyrrolidone N-methyl-2-pyrrolidone N-hydroxyethyl-2-pyrrolidone N-methyl-2-piperidone 2-ϵ-caprolactam, N-methyl-2-caprolactam, 2-piperidone (or 2-δ-valerolactam) or N-(4-hydroxybenzyl)pyrrolidone.

Also disclosed is a method for the selective extraction of nucleic acid from a complex biological sample comprising lysing the sample in a guanidine thiocyanate buffer; combining the sample with an extraction solution containing a lactam and phenol to create a first aqueous phase and a first organic phase; and isolating DNA from the first aqueous phase. Ribosomal RNA (rRNA) may further be isolated from the first organic phase by adding a buffer solution to the first organic phase, heating the first organic phase and buffer solution mixture to create a second organic phase and a second aqueous phase, and extracting rRNA from the aqueous phase.

Further disclosed is a method for the selective extraction of plasmid DNA from a complex biological sample comprising partially solubilizing cells in the sample in a weak chaotropic salt solution such as one containing guanidine hydrochloride (GnHCl), removing insoluble material from the solution and then extracting plasmid DNA from the solution.

Additionally, hybridization assays are disclosed wherein a sample containing a complex biological mixture of nucleic acids and non-nucleic acids is combined with an extraction solution comprising a lactam, isolating nucleic acid from the resulting combined solution and then a hybridization assay is conducted with the isolated nucleic acid.

The lactams used in the present invention are of a very low order toxicity and are not corrosive to human tissue. They retain most of the solvent properties of phenol or phenol/chloroform and are uniquely suited to the application of nucleic acid isolation and/or fractionation of biological macromolecular complexes. In addition they are substantially less expensive than the commonly employed organic solvents. Extraction by cesium chloride and alcohol precipitation may also be avoided through the use of the methods of the present invention, thus eliminating exposure to toxic cesium chloride. The extraction methods of the present invention are faster, simpler, safer and more sensitive than methods previously used in the extraction of nucleic acid. Thus, they represent a significant advance in the field providing a means for scaling up the extraction of desired nucleic acids.

The use of lactams avoids problems relating to the incompatibility of chaotropes with ionic detergents during isolation of nucleic acids from chaotropic salt solutions. The use of lactams also avoids difficulties arising during the partitioning of nucleic acid into an aqueous phase, given the high molar concentrations of salt typically used and the chaotropic behavior of these salts. The use of lactams in extraction techniques involving chaotropic salts allows the rapid and simple recovery of intact RNA, DNA, or total nucleic acid.

An alternative method is also disclosed which allows the extraction of nucleic acid without using heat. This method provides for the extraction of nucleic acid from a complex biological sample by combining the sample with an extraction solution containing a guanidine salt then adding a component selected from the group consisting of alcohols polysaccharide sulfates and polymeric sulfonic acids. rendering the solution biphasic and isolating the nucleic acid from the aqueous phase.

DESCRIPTION OF THE FIGURE

The Figure illustrates various known synthetic pathways for the production of lactams.

FIG. 1A$_1$ schematically shows a means for substituting an alkali metal derivative of pyrrolidone without opening the lactam ring:

FIG. 1A$_2$ illustrates reaction of a lactam and an acid anhydride, forming an N-acyl lactam:

FIG. 1A$_3$ represents reaction of 2-pyrrolidone and ethylene oxide to form substituted 2-pyrrolidone:

FIG. 1A$_4$ schematically shows reaction of butyrolactone in the presence of ammonia and heat to yield 2-pyrrolidone: and FIG. 1A$_5$ indicates pyrolysis of an amino acid to yield a lactam.

FIG. 1B$_1$ illustrates reaction of butyrolactone and an alkylamine to yield an alkyl substituted lactam: and FIG. 1B$_2$. Method G represents reaction of hydrazoic acid and a cyclic ketone to yield the corresponding lactam, where FIG. 1B$_2$ includes general instructions for making various lactams according to Method G.

DETAILED DESCRIPTION

This invention relates to novel means and methods for the extraction of nucleic acid from a complex biological mixture containing nucleic acids and non-nucleic acids. Highly sensitive hybridization assays are also described. The methods of the present invention enable one to easily process a biological sample containing nucleic acids by promoting the lysis of cells in the sample and promoting the extraction of nucleic acids being present in the cells. The methods of the present invention further enable one to readily assay for a nucleic acid suspected of being present in cells. i.e., a target nucleic acid. The extraction methods include lysing the cells in a solution comprising a lactam and then isolating the nucleic acid.

The extraction and hybridization methods of the present invention may be applied to a complex biological mixture of nucleic acid (RNA and/or DNA) and non-nucleic acid. Such a complex biological mixture includes a wide range of eucaryotic and procaryotic cells, including protoplasts; or other biological materials which may harbor nucleic acids. The methods are thus applicable to tissue culture animal cells, animal tissue (e.g., heart, liver or brain, homogenized in lysis buffer), blood cells, reticulocytes, lymphocytes, plant cells or other cells sensitive to osmotic shock and cells of bacteria, yeasts, viruses, mycoplasmas, protozoa, rickettsia, fungi and other small microbial cells and the like.

The assay and isolation procedures of the present invention are useful, for instance, for detecting nonpathogenic or pathogenic microorganisms of interest. By extracting nucleic acid and detecting specific hybridization between nucleotide probes of a known source and nucleic acids resident in the biological sample, the presence of the microorganisms may be established. Biological samples of interest could include virtually any type of specimen which may contain microorganisms of interest.

The nucleic acid sample to be assayed or to serve as a source for the extraction of nucleic acids is combined with an extraction solution comprising a lactam. Lactams are a class of a group of organic cyclic compounds containing the —NH—CO— group in the ring. Such compounds are typically formed by the elimination of water from the amino and carboxyl groups of a noncyclic compound. The particular substituents on the lactam ring are not critical to this invention. It is, however, important that the lactam maintain hydrogen bonding capacity, water solubility and the ability to form biphasic solutions upon heating or the addition of appropriate organic molecules. Thus, substituents of more than eight carbons, for example, would be less preferred than substituents with less than eight carbons which would be more water soluble. This is especially true if the preferred substituents contain additional polar groups.

Preferably, the lactam will be of the general formula including racemic mixtures and optically active isomers:

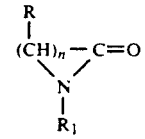

wherein n=3 to 8 (with the total number of R substituents being 3 to 8), and R$_1$ is selected from the group consisting of:
hydrogen,
alkyl of 1 to 20 carbons,
aryl of 6 to 10 carbons,
arylalkyl of 7 to 20 carbons,
alkylcarboxyamide of 1 to 20 carbons,
hydroxyarylalkyl of 7 to 20 carbons,
N-mono-substituted alkylcarboxyamide,
N,N-dialkyl-substituted alkylcarboxyamide,
alkylcarboxylate of 2 to 20 carbons,
acyl of 2 to 20 carbons,
cycloalkane of 4 to 20 carbons,
hydroxyalkyl,
and cyanoalkyl:
and where the R substituents can be the same or different and selected from a group consisting of hydrogen halogen and alkyl of 1 to 5 carbons such that the total carbon number for all R substituents does not exceed 20; with the further provision that the total carbon number of the R$_1$ substituent does not exceed 20 and where at least one R designated substituent is hydrogen.

Pyrrolidones, piperidones and caprolactams are lactams which are particularly preferred. The lactams which are preferred also include those where n = 3 to 6; where at least one R substituent is methyl; where the $R_1$ substituent and all of the R substituents are hydrogen; where the $R_1$ substituent is other than hydrogen and the R substituents are both hydrogen; where the $R_1$ substituent is a cycloalkane of 4 to 7 carbons; where the $R_1$ substituent is $-CH_2-CH_2OH$; where the $R_1$ substituent is $-CH_2-CH_3$; where the $R_1$ substituent is methyl; or where the $R_1$ substituent is dodecyl. Examples of these preferred lactams which are most preferred are 2-pyrrolidone, N-methyl-2-pyrrolidone, N-hydroxyethyl-2-pyrrolidone, N-cyclohexyl-2-pyrrolidone, N-dodecyl-2-pyrrolidone, N-ethyl-2-pyrrolidone, N-methyl-2-piperidone, 2-ε-caprolactam, N-methyl-2-caprolactam, N-4-hydroxybenzyl)pyrrolidone and 2-piperidone (or 2-δvalerolactam). These are commercially available from the GAF Chemicals Corporation (a subsidiary of GAF Corporation. Wayne, N.J.) and/or Aldrich Chemical Company (Milwaukee, Wis.).

Alkyl refers to an aliphatic hydrocarbon radical, $-(CH_2)_nCH_3$, either branched or unbranched such as methyl, ethyl, n-propyl, isopropyl, n-butyl, isobutyl, sec-butyl, tert-butyl, dodecyl or the like.

Aryl refers to a radical derived from an aromatic hydrocarbon by removal of one hydrogen atom such as phenyl, α-napthyl, β-napthyl, biphenyl, anthryl and the like.

Arylalkyl, $-(CH_{2n}-Ar$, refers to an alkyl radical as defined above joined to an aryl radical.

Alkylcarboxyamide refers to a radical, $-(CH_2)_n-CONH_2$.

Hydroxyarylalkyl refers to an arylalkyl radical where the aryl radical is an hydroxyaryl.

N-mono-substituted alkylcarboxyamide refers to a radical.

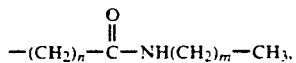

where n = 10 to 20 carbons and m = 1 to 5 carbons.

N,N-dialkyl-substituted alkylcarboxyamide refers to a radical,

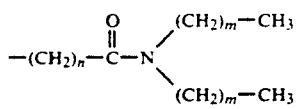

where each alkyl can be the same or different and where n = 10 to 20 carbons and m = 1 to 5 carbons.

Alkylcarboxylate refers to a radical $-(CH_2)_nCOO^-$, where n preferably = 1 to 19 carbons.

Acyl includes any organic radical derived from an organic acid, such as a carboxylic acid by elimination of the hydroxyl group. It is represented by the formula $R_6-CO$, wherein $R_6$ can be as defined in U.S. Pat. No. 4,665,067 at column 2, line 31 through column 12, line 32, which is incorporated by reference herein. It is preferred that $R_6$ be an alkyl of 1 to 20 carbons or a cycloalkyl.

Hydroxyalkyl refers to a radical $-(CH_2)_nOH$, where n = 1 to 20.

Cycloalkane or cycloalkyl refers to a radical of a saturated hydrocarbon in a ring structure such as cyclopropyl, cyclobutyl, cyclopentyl, cyclohexyl, cycloheptyl, adamantyl and the like.

Cyanoalkyl refers to a radical of a cyano group, having the formula $-C\equiv N$ above.

Unless otherwise stated, all number ranges are inclusive of the stated range (e.g., 1 to 5 carbons includes and 5 carbons).

Halogen refers to chlorine, bromine, fluorine and iodine.

Various pyrrolidone derivatives may be prepared as described in Kirk-Othmer Encyclopedia of Chemical Technology 19:510-518 (1982), incorporated by reference herein, or as follows:

Alkali metal derivatives of pyrrolidone are readily formed by reaction with metal or from concentrated caustic soda and 2-pyrrolidone in acetone solution as described in "Acetylene Chemistry," J. W. Reppe, P. B. Report, 18-852-s. C.A. Meyer & Co., Inc., New York, N.Y. (1949), 210 pp., incorporated by reference herein. Such procedure permits reaction with substituted alkyl, aryl or arylalkyl halides without opening the lactam ring to give N-alkyl, N-aryl or N-arylalkyl pyrrolidones. See Method A on FIG. 1A. The latter two can be nitrated without rupture of the lactam ring and alkyl, hydroxy, alkoxy, or halogen substitution is also possible. N-octyl-2-pyrrolidone and N-dodecyl-2-pyrrolidone are synthesized in this manner and belong to the N-alkyl-2-pyrrolidone family. N-methyl-2-pyrrolidone, the lactam of 4-methylaminobutyric acid, is synthesized using the Reppe chemistry described above. Acylated lactams can also be chlorinated and brominated at elevated temperatures under the influence of light.

Lactams can react with the following reagents:
a) Acid anhydrides or chlorides result in formation of N-acyl lactams; for example acetic anhydride forms from N-acetyl-2-pyrrolidone. See Method B on FIG. 1A.
b) N-methylol-2-pyrrolidone results from reaction of formaldehyde and 2-pyrrolidone.
c) N-(2-hydroxymethyl)-2-pyrrolidone is formed by reaction with ethylene oxide. See Method C on FIG. 1A.

Other examples of various synthesis routes are also set forth on FIG. 1. Method D on FIG. 1A shows the reaction of butyrolactone in the presence of a moderate excess of ammonia under heat to yield 2-pyrrolidone. Method F on FIG. 1B shows the same reaction using butyrolactone and alkylamine as the starting materials to yield an alkyl substituted lactam.

Method E on FIG. 1A shows that lactams are easily produced from the pyrolysis of amino acids. The reaction of hydrazoic acids with cyclic ketones yield the corresponding lactam as shown in method G on FIG. 1B. The commercially available technical grades of all pyrrolidones should be vacuum distilled prior to use with biological samples.

The lactams should be provided in concentrations in excess of about 5% of the total volume of the extraction solution up to a concentration of about 70%, preferably a concentration of 20% to 50%, most preferably a concentration of about 30% to 50%. The lactams may be used singly or in combination.

Traditionally, organic solvents, such as phenol or a phenol-chloroform combination are used to extract nucleic acid, using a phase separation. These methods may be used effectively with the extraction solutions of the present invention; however, an advantage of the methods of the present invention is that such toxic and tedious extraction methods are not necessary.

Extraction of Total Nucleic Acid

The lactam-containing extraction solutions of the present invention permit the complete extraction of total nucleic acid (DNA and RNA). The lactam-containing extraction solution is combined with the complex biological mixture so that the combined solution becomes biphasic with the non-nucleic acid material present in the organic phase and the nucleic acid solution present in the aqueous phase. The combined solution is typically mixed and subjected to centrifugation and the nucleic acid in the aqueous phase is precipitated with ethanol.

The lactam-containing extraction solution will become biphasic upon mixing with the nucleic acid sample. If the lactam is miscible with water, such as N-hydroxyethyl-2-pyrrolidone, then a biphasic state may be created upon mixing the extraction solution with the nucleic acid sample and heating the combined solution, typically to a temperature greater than 40° C., usually to a temperature of about 45° C. until the solution becomes biphasic. If the lactam is immiscible with water, such as N-dodecyl-2-pyrrolidone or N-octyl-2-pyrrolidone, then a biphasic state is created without heat. Addition of other organic solvents, such as phenol, to the extraction solution will also create a biphasic state for extraction. The extraction solution will typically be combined with the nucleic acid sample so that the concentration of lactam (or lactam and organic solvent) in the biphasic solution is about 30-50%.

The extraction procedure will preferably use a complex biological sample of a concentration such that after combining the sample with the extraction solution, the amount of nucleic acid present in the aqueous phase will not be in excess of 1 mg/ml or such that the total cellular material does not exceed 50 mg/ml.

Preferably, the extraction solution will contain standard buffers and detergents to promote lysing of cells. A buffer such as sodium citrate, Tris HCl, PIPES or HEPES, preferably Tris-HCl at a concentration of about 0.05 to 0.1M can be used. The extraction solution will typically also contain about 0.05 to 0.5% of an ionic or nonionic detergent, such as sodium dodecylsulfate (SDS) or Sarkosyl (Sigma Chemical Co., St. Louis, Mo.) and between 1 to 10 mM EDTA.

Chaotropic agents which disturb the secondary and tertiary structure of proteins, for example, guanidine salts such as guanidine hydrochloride (GnHCl) and thiocyanate or urea, lithium chloride and other thiocyanates may be used in combination with the lactams to dissociate nucleic acids and inhibit nucleases. The use of chaotropic agents in the extraction and hybridization of nucleic acids is described in E.P. Publication No. 0 127 327, which is incorporated by reference herein.

Extraction of total nucleic acid without the use of heat may alternatively be performed by using a guanidine-based chaotrope such as GnHCl which does not contain the SCN anion. The complex biological sample may be lysed first with an extraction solution comprising GnHCl and then contacted with an extraction solution comprising a lactam, preferably N-methyl-2-pyrrolidone. The extraction solution containing the lactam may then be made biphasic by the addition of an organic solvent such as phenol or chloroform. Total nucleic acid is isolated from the aqueous phase.

Lactam-free Extraction Without Heat

An alternative effective approach to using lactams in extracting total nucleic acid from complex biological samples, which surprisingly may be accomplished without heat is the use of certain competitive agents from the group consisting of alcohol, polysaccharide sulfate, and polymeric sulfonic acid in conjunction with guanidine salt lysing agents. After solubilizing the complex biological sample with a solution comprising the guanidine salt, the competitive agent is added at a molarity approximately comparable to or in excess of the guanidine salt. The extraction solution is made biphasic by the addition of an organic solvent such as lactam, phenol or chloroform and nucleic acid is isolated from the aqueous phase. No heat needs to be used in this extraction process. This process is particularly beneficial when GnSCN is used as the lysing agent.

The competitive agent alcohols are selected from the group consisting of monohydroxyalkanes, dihydroxyalkanes, trihydroxyalkanes with a total carbon number not exceeding 20, monosaccharides, oligosaccharides, polysaccharides, monohydroxycycloalkanes, dihydroxycycloalkanes, trihydroxycycloalkanes and polyhydroxycycloalkanes. Preferably the alcohol will be a dihydroxyalkane, most preferably ethylene glycol. The competitive agent polysaccharide sulfates will preferably be salts of polysaccharide chains of about 1.500 to 15,000 daltons, most preferably dextran sulfate.

The competitive agent polymeric sulfonic acid is a sulfonic acid ranging from about 10,000 to 500,000 daltons. Preferably the polymeric sulfonic acid is one which has subunits having the general formula:

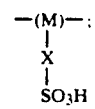

where M is a backbone component; and X is a spacer group. The backbone may comprise linear monomers, ringed monomers, branched monomers or a combination of these monomers which are linked together into a polymer. The term monomer is used here to refer to a subunit, and does not imply that the monomer necessarily be polymerizable with the spacer and sulfate group in the final form present in the polymer. Appropriate backbones often substituted, include polyethylene, polyacrylate chains, polyamide chains, polyacrylamide, polypeptides, or polysaccharides.

The hydrocarbon polymer backbone will preferably be linear, but may contain branched structures. Polymer lengths in the range of 1,500 to 20,000 daltons are preferred. Polymers may be primarily homopolymers, and these homopolymers might be linked together by identical (e.g. head to tail) or nonidentical (e.g. head to head and tail to tail) linkages. Alternatively, the polymers may comprise heterogenous subunits, or be composed of combinations of various different types of subunits (e.g. copolymers), in an ordered or random sequence. The spacers will be hydrocarbon moieties. Typical spacers include saturated or unsaturated alkyl groups, e.g., methylene, ethylene and other alkyl groups, substituted phenyl groups, e.g., 1,2 (ortho), 1,3 (meta) or 1,4 (para), benzyl groups, or naphthyl groups. The spacers can be linear, branched or ringed structures.

Polyvinylsulfonic acid (PVSA) and polystyrene sulfonic acid (PSSA) are the polymeric sulfonic acids most preferred.

Sequential Selective Extraction of DNA and rRNA

Extraction solutions of the present invention also permit the selective and sequential extraction of DNA and rRNA. A complex biological sample is first lysed in a guanidine thiocyanate buffer solution, such as a 3M GnSCN solution. The lysed sample is then combined with an extraction solution containing a lactam and phenol to create a first aqueous phase and a first organic phase. A room temperature extraction is performed where DNA is isolated from the first aqueous phase, the rRNA remaining in the first organic phase. The rRNA is isolated from the first organic phase after a standard buffer solution, such as 1% SDS, 50 mM Tris, 25 mM EDTA and 0.05M NaCl. This solution is heated, typically to about 65° C. to create a second organic phase and a second aqueous phase. The rRNA is then isolated from the second aqueous phase.

For the sequential DNA-rRNA isolation, it is preferred that the molar ratio of GnSCN to lactam be about 1 to 3, and that the concentration of lactam to phenol range from about 1:1 to about 1:5 or to about 5:1. The lactam of preference for this procedure is N-methyl-2-pyrrolidone. See Example VIII for further illustration.

Selective Extraction of Plasmid DNA

Plasmid DNA may also be selectively isolated from complex biological samples using the extraction methods of the present invention. For example, methods to partially solubilize cells so that chromosomal DNA is retained in the cell and plasmid DNA is leaked into solution may be used. Weak chaotropic salt solutions such as GnHCl, guanidine sulfate, or guanidine carbonate, containing non-ionic detergents, may be used to cause cells, particularly bacterial cells, to leak plasmid DNA. The weak chaotropic salt solution will preferably contain the chaotropic agent at a molar concentration of about 0.1 to 2M. The cells containing the chromosomal DNA may then be removed from the solution containing the plasmid DNA, such as by centrifugation, filtration or dialysis. The plasmid DNA may then be extracted from the solution by any methods known in the art or preferably by the extraction methods disclosed herein. See Example IX for further illustration. It will be obvious to those skilled in the art that other methods for isolating plasmid DNA may be used in conjunction with the extraction solutions disclosed herein such as those found in *Methods in Molecular Biology, Vol. II*, "Nucleic Acids," Humana Press, Clifton, N.J. (1984) p.177-189, which is incorporated by reference herein.

Extraction to Improve Hybridization

It may also be advantageous to use the extraction methods and solutions of this invention prior to conducting a hybridization assay on a complex biological sample such as on feces or blood. The extraction procedure may be necessary in some cases to remove contaminants which contribute to background interference. Extraction followed by procedures to concentrate the nucleic acid may improve sensitivity and the signal to noise ratio in hybridization assays. Hybridization assays of particular interest include those set forth in commonly assigned U.S. application No. 07/384,230, filed the same date hereof, abandoned in favor of continuation-in-part U.S. application Ser. No. 07/558,896, now U.S. Pat. No. 5,106,730.

Conducting a hybridization assay according to the present invention can be performed by any method known to those skilled in the art or analogous to immunoassay methodology given the guidelines presented herein. Preferred methods of assay are the sandwich assays and variations thereof and the competition or displacement assay. Hybridization techniques are generally described in "Nucleic Acid Hybridization. A Practical Approach," Ed. Hames, B. D. and Higgins, S. J., IRL Press, 1985; Gall and Pardue (1969), *Proc. Natl. Acad. Sci., U.S.A.*, 63:378-383; and John, Burnsteil and Jones (1969) Nature, 223:582-587. As improvements are made in hybridization techniques, they can readily be applied.

Sandwich assays are commercially useful hybridization assays for detecting or isolating nucleic acid sequences. Such assays utilize a "capture" nucleic acid covalently immobilized to a solid support and labelled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

In a hybridization assay, the target nucleic acid is the nucleotide sequence of deoxyribonucleic acid (DNA). ribonucleic acid (RNA) or ribosomal ribonucleic acid (rRNA) whose presence is of interest and whose presence or absence is to be detected for. The target nucleic acid may be provided in a complex biological mixture of nucleic acid (RNA. DNA and/or rRNA) and non-nucleic acid.

The target nucleic acids of primary preference are RNA molecules and, in particular, open regions of rRNA which have minimal secondary or tertiary interactions with adjacent nucleotides, such as on the 16s or 23s rRNA as described in commonly assigned U.S. patent application No. 142,106, which is incorporated by reference herein. If target nucleic acids of choice are double stranded or otherwise have significant secondary and tertiary structure, they may need to be heated prior to hybridization. In this case, heating may occur prior to or after the introduction of the nucleic acids into the hybridization medium.

A nucleic acid substantially complementary to the target nucleic acid will be introduced in the hybridization process. "A nucleic acid substantially complementary to the target nucleic acid" is a polynucleotide or oligonucleotide containing naturally occurring nucleotides or their analogs, such as 7-deazaguanosine or inosine, sufficiently complementary to hybridize with the target nucleic acid such that stable and specific binding occurs between the target and the complementary nucleic acid. Therefore, the complementary nucleic acid sequence need not reflect the exact sequence of the target nucleic acid. For example, a non-complementary nucleotide fragment may be attached to a complementary nucleotide fragment or alternatively, non-complementary bases or longer sequences can be interspersed into the complementary nucleic acid, provided that the complementary nucleic acid sequence has sufficient complementarity with the sequence of the target nucleic acid to hybridize therewith forming a hybridization complex and further is capable of immobilizing the target nucleic acid to a solid support. The degree of homology required for formation of a stable hybridization complex (duplex) varies with the stringency of the hybridization medium and/or wash medium. Oligonucleotide probes to rRNA are most preferred such as those described in commonly assigned U.S. patent application Ser. No. 142,106, which is incorporated by reference herein. The complementary nucleic acid may be present in a pre-prepared hybridization media or introduced at some later point prior to hybridization.

The hybridization media and processes disclosed herein, however, are uniquely suited to a one-step assay. The media may be pre-prepared, either commercially or in the laboratory to contain all the necessary components for hybridization. For instance, in a sandwich assay the media could comprise a lactam, desired buffers and detergents, a capture nucleic acid bound to a solid support such as a microbead, and a signal nucleic acid. This media then need only be combined with the sample containing the target nucleic acid at the time the assay is to be performed. Once hybridization occurs the hybridization complex attached to the solid support may be washed and the extent of hybridization determined.

Virtually any solid surface can be used as a support for hybridization assays, including metals and plastics. Two types of solid surfaces are generally available namely:

a) Membranes, polystyrene beads, nylon, teflon, polystyrene/latex beads, latex beads or any solid support possessing an activated carboxylate, sulfonate, phosphate or similar activatable group are suitable for use as solid surface substratum to which nucleic acids or oligonucleotides can be immobilized.

b) Porous membranes possessing pre-activated surfaces which may be obtained commercially (e.g., Pall Immunodyne Immunoaffinity Membrane, Pall BioSupport Division, East Hills, N.Y., or Immobilon Affinity membranes from Millipore, Bedford, Mass.) and which may be used to immobilize capture oligonucleotides. Microbeads, including magnetic beads, of polystyrene, teflon, silica, nylon or latex are particularly useful.

Capture or signal nucleic acids for use in hybridization assays can be obtained from the entire sequence or portions thereof of an organism's genome, from messenger RNA, or from cDNA obtained by reverse transcription of messenger RNA. After isolation of genomic DNA or cDNA fragments, the fragments are typically inserted into a replication vector, such as lambda phage, pBR322, M13, or vectors containing the SP6 or T7 promoter and cloned as a library in a bacterial host. Following appropriate screening procedures, a recombinant vector with the desired probe insert is isolated and labelled as described below. The vector is then grown in a suitable host. The probe and its vector are purified from the host cells by cell lysis and nucleic acid extraction. Following isolation, the probe can be purified away from the vector by digestion with selected restriction enzymes and sequenced. Further isolation of the probe can be achieved by using gel electrophoresis or high pressure liquid chromatography.

Once the appropriate sequences are determined, DNA probes are preferably chemically synthesized using commercially available methods and equipment. For example, the solid phase phosphoramidite method can be used to produce short probes of between 15 and 50 bases and have a molecular weight of less than 16,000 daltons, (Caruthers et al., *Cold Spring Harbour Symp.* *Quant. Biol.*, 47:411–418 (1982), and Adams et al., *J. Am. Chem. Soc.*, 105:661 (1983).

When synthesizing a probe for a specific target, the choice of nucleotide sequence will determine the specificity of the test. For example, by comparing DNA sequences from several virus isolates, one can select a sequence for virus detection that is either type specific or genus specific. Comparisons of DNA regions and sequences can be achieved using commercially available computer programs.

The determination of the extent of hybridization may be done by any of the methods well-known in the art. If there is no detectable hybridization, the extent of hybridization is thus 0. Typically labelled signal nucleic acids are used to detect hybridization. Complementary nucleic acids or signal nucleic acids may be labelled by any one of several methods typically used to detect the presence of hybridized polynucleotides. The most common method of detection is the use of autoradiography with $^{3}H$, $^{125}I$, $^{35}S$, $^{14}C$, or $^{32}P$ labelled probes or the like. The choice of radioactive isotope depends on research preferences due to ease of synthesis, varying stability, and half lives of the selected isotopes. Other labels include ligands which bind to labelled antibodies, fluorophores, chemiluminescent agents, enzymes, and antibodies which can serve as specific binding pair members for a labelled ligand. The choice of label depends on sensitivity required, ease of conjugation with the probe, stability requirements, and available instrumentation.

The choice of label dictates the manner in which the label is bound to the probe. Radioactive probes are typically made using commercially available nucleotides containing the desired radioactive isotope. The radioactive nucleotides can be incorporated into probes by several means such as by nick translation of double-stranded probes; by copying single-stranded M13 plasmids having specific inserts with the Klenow fragment of DNA polymerase in the presence of radioactive dNTP; by transcribing cDNA from RNA templates using reverse transcriptase in the presence of radioactive dNTP; by transcribing RNA from vectors containing SP6 promoters or T7 promoters using SP6 or T7 RNA polymerase in the presence of radioactive rNTP; by tailing the 3' ends of probes with radioactive nucleotides using terminal transferase; or by phosphorylation of the 5' ends of probes using [$^{32}P$]-ATP and polynucleotide kinase.

Non-radioactive probes are often labelled by indirect means. Generally, a ligand molecule is covalently bound to the probe. The ligand then binds to an anti-ligand molecule which is either inherently detectable or covalently bound to a signal system, such as a detectable enzyme, a fluorescent compound, or a chemiluminescent compound. Ligands and anti-ligands may be varied widely. Where a ligand has a natural anti-ligand, for example, biotin, thyroxine, and cortisol, it can be used in conjunction with the labelled, naturally occurring anti-ligands. Alternatively, any haptenic or antigenic compound can be used in combination with an antibody.

Probes can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, AMPPD ([3-(2'-spiroamantane)-4-methoxy-4-(3'phosphoryloxy)-phenyl-1.2-dioxetane]) and 2,3-dihydrophthalazinediones, e.g., luminol.

The amount of labelled probe which is present in the hybridization medium or extraction solution may vary widely. Generally, substantial excesses of probe over the stoichiometric amount of the target nucleic acid will be employed to enhance the rate of binding of the probe to the target DNA. Treatment with ultrasound by immersion of the reaction vessel into commercially available sonication baths can often times accelerate the hybridization rates.

After hybridization at a temperature and time period appropriate for the particular hybridization solution used, the glass, plastic, or filter support to which the capture nucleic acid-target nucleic acid hybridization complex is attached is introduced into a wash solution typically containing similar reagents (e.g., sodium chloride, buffers, organic solvents and detergent), as provided in the hybridization solution. These reagents may be at similar concentrations as the hybridization medium, but often they are at lower concentrations when more stringent washing conditions are desired. The time period for which the support is maintained in the wash solutions may vary from minutes to several hours or more.

Either the hybridization or the wash medium can be stringent. After appropriate stringent washing, the correct hybridization complex may now be detected in accordance with the nature of the label.

The probe may be conjugated directly with the label. For example, where the label is radioactive, the probe with associated hybridization complex substrate is exposed to X-ray film. Where the label is fluorescent, the sample is detected by first irradiating it with light of a particular wavelength. The sample absorbs this light and then emits light of a different wavelength which is picked up by a detector (*Physical Biochemistry*, Freifelder, D., W. H. Freeman & Co. (1982), pp. 537–542). Where the label is an enzyme, the sample is detected by incubation on an appropriate substrate for the enzyme. The signal generated may be a colored precipitate, a colored or fluorescent soluble material, or photons generated by bioluminescence or chemi-luminescence. The preferred label for probe assays generates a colored precipitate to indicate a positive reading. For example, alkaline phosphatase will dephosphorylate indoxyl phosphate which then will participate in a reduction reaction to convert tetrazolium salts to highly colored and insoluble formazans.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label. (Tijssen, P., "Practice and Theory of Enzyme Immunoassays," *Laboratory Techniques in Biochemistry and Molecular Biology*, Burdon, R. H., van Knippenberg, P. H., Eds., Elsevier (1985). pp. 9–20.)

Kits for the extraction of and hybridization of nucleic acids are also contemplated. Such kits would contain at least one vial containing an extraction solution or a hybridization medium which comprises a lactam at a concentration in excess of 5%. Detergents, buffer solutions and additional vials which contain components to detect target nucleic acids may also be included.

The following examples are offered by way of illustration and are not to be construed as limiting the invention, as claimed, in any way.

EXAMPLE I

Lysis of Bacterial and Human Cells with Pyrrolidone-Based Solutions

A pre-prepared lysis solution composed of 20% N-cyclohexyl-2-pyrrolidone, and 20% N-hydroxymethyl-2-pyrrolidone, (both obtained from GAF Chemicals Corporation, Wayne, N.J.), 50 mM Tris, pH 7.6, 25 mM EDTA, and 2% SDS (sodium dodecyl sulfate) was used to lyse $1 \times 10^9$ cells of *Actinobacillus actinomycetecomitans* ("Aa"), *Bacteroides intermedius* ("Bi"), *Eikenella corrodens* ("Ec"), *Wolinella recta* ("Wr"), *Fusobacterium nucleatum* ("Fn"), *Bacteroides gingivalis* ("Bg"), and $1 \times 10^6$ cells of HeLa in 100 microliter volumes each. The solution was noted to clear within 10 seconds and phase contrast microscopy indicated the solubilization of all the cell types tested. No intact cell shapes were observed by light microscopy. In addition, the lysates were observed by fluorescence microscopy in which ethidium bromide was added to the lysate at a concentration of 0.5 micrograms per ml. Only extremely diffuse staining was observed in all lysates compared to intact cell controls, indicating that lysis was complete and that chromosomal DNA was unfolded and released from the cells.

EXAMPLE II

Lysis of Bacterial and Human Cells with Pyrrolidone-Based Solutions Containing a Chaotropic Agent A lysis solution composed of 20% N-cyclohexyl-2-pyrrolidone, 20% N-hydroxymethyl-2-pyrrolidone, 10% N-dodecyl-2-pyrrolidone, 1M Guanidine-HCl, 50 mM Tris, pH 7.6, 25 mM EDTA, and 2% SDS was used to lyse $1 \times 10^9$ cells of Aa, Bi, Ec, Wr, Fn, Bg, and $1 \times 10^6$ cells of HeLa in 100 microliter volumes. The solution was noted to clear within 10 seconds and phase contrast microscopy indicated the solubilization of all the cell types tested. No intact cell shapes were observed by light microscopy. In addition, the lysates were observed by fluorescence microscopy in which ethidium bromide was added to the lysate at a concentration of 0.5 micrograms per ml. Only extremely diffuse staining was observed in all lysates compared to intact cell controls, indicating that lysis was complete and that chromosomal DNA was unfolded and released from the cells.

EXAMPLE III

Combination Pyrrolidone-Based Hybridization Solutions Promote Specific Nucleic Acid Base Pairing A solution composed of 20% N-cyclohexyl-2-pyrrolidone, 20% N-hydroxymethyl-2-pyrrolidone, 50 mM Tris pH 7.6, 25 mM EDTA and 1% SDS was used to test the ability of $^{32}$P-labelled specific oligonucleotide probes (synthetic oligonucleotide probes in which the sequence is complementary to unique hypervariable regions of the 16s rRNA of the respective bacterium) to hybridize specifically to total nucleic acid from Aa, Bg, Bi, Ec, Fn, Wr and E. coli immobilized on Nytran filters (Schleicher and Schuell, Keene, N.H.). Approximately 50 nanograms of total nucleic acid was immobilized on each nytran slot, $6.5 \times 10^6$ cpm of $^{32}$P labelled probe (approximately 65 nanograms) of Aa complementary probe (Aa4B) was added to 1 ml of the solution described above and incubated with nytran filter strips containing Aa, Bg, Bi, Ec, Fn, Wr, and E. coli slots of nucleic acid. Hybridization was allowed to proceed for 3 hours at 19° C. The filters were washed with 0.09M NaCl, 50 mM Tris pH 7.6, 25 mM EDTA and 0.1% SDS at 50° C. and radioactivity was then detected by fluorometry. Results indicated that the Aa probes hybridized only with Aa total nucleic acid, demonstrating that the pyrrolidone solution promoted specific nucleic acid base pairing. Identical results were obtained using solutions of the same composition described above with the exception of altering each pyrrolidone concentration to 15% or 25% respectively.

EXAMPLE IV

Individual Pyrrolidone-Based Hybridization Solutions Promote Specific Nucleic Acid Base Pairing A solution composed of 40% N-cyclohexyl-2-pyrrolidone, or 40% N-hydroxymethyl-2-pyrrolidone, or 40% N-methyl-2-pyrrolidone, 50 mM Tris pH 7.6, 25 mM EDTA and 1% SDS was used to test the ability of $^{32}$P-labelled specific oligonucleotide probes (synthetic oligonucleotide probes in which the sequence is complementary to unique hypervariable regions of the 16s rRNA of the respective bacterium) to hybridize specifically to total nucleic acid from Aa, Bg, Bi, Ec, Fn, Wr, and E. coli immobilized on Nytran filters. Approximately 50 nanograms of total nucleic acid was immobilized on each nytran slot, $6.5 \times 10^6$ cpm of $^{32}$P-labelled probe (approximately 65 nanograms) of Aa complementary probe (Aa4B) was added to 1 ml of the solution described above and incubated with nytran filter strips containing Aa, Bg, Bi, Ec, Fn, Wr, and E. coli slots of nucleic acid. Hybridization was allowed to proceed for 3 hours at 19° C. The filters were washed with 0.09M NaCl, 50 mM Tris pH 7.6, 25 mM EDTA and 0.1% SDS (SDS/FW) at 50° C. and radioactivity was then detected by fluorometry. Results indicated that the Aa probes hybridized only with Aa total nucleic acid demonstrating that the individual pyrrolidone solutions promoted specific nucleic acid base pairing. Identical results were obtained using solutions of the same composition described above with the exception of altering the individual pyrrolidone concentration to 30% or 50%, respectively.

EXAMPLE V

Individual Pyrrolidone-Based Hybridization Solutions Containing Chaotropic Agents, Piperidone-Based Hybridization Solutions and Caprolactam or Calerolactam-Based Hybridization Solutions Promote Specific Nucleic Acid Base Pairing A solution composed of 35% N-methyl-2-piperidone, or 35% 2-ε-caprolactam, or 35% N-methyl-2-caprolactam, or 35% 2-δ-valerolactam, 50 mM Tris pH 7.6, 25 mM EDTA and 1% SDS or a solution containing 20% N-cyclohexyl-2-pyrrolidone, 20% N-hydroxyethyl-2-pyrrolidone, 5% N-dodecyl-2-pyrrolidone, 1M guanidine-HCl, 50 mM Tris pH 7.6, 25 mM EDTA and 2% SDS, or a solution containing 20% N-cyclohexyl-2-pyrrolidone, 20% N-hydroxyethyl-2-pyrrolidone, 5% N-dodecyl-2-pyrrolidone, 0.5M guanidine HCl, 50 mM Tris pH 7.6, 25 mM EDTA and 2% SDS, was used to test the ability of $^{32}$P-labelled specific oligonucleotide probes (synthetic oligonucleotide probes in which the sequence is complementary to unique hypervariable regions of the 16s rRNA of the respective bacterium) to hybridize specifically to total nucleic acid from Aa, Bg, Bi, Ec, Fn, Wr, and E. coli immobilized on Nytran filters. Approximately 50 nanograms of total nucleic acid was immobilized on each nytran slot, $6.5 \times 10^6$ cpm of P32-labelled probe (approximately 65 nanograms) of Bg complementary probe (Bg5B) was added to 1 ml of the solution described above and incubated with nytran filter strips containing Aa, Bg, Bi, Ec, Fn, Wr, and E. coli slots of nucleic acid. Hybridization was allowed to proceed for 3 hours at 19° C. The filters were washed with 0.09M NaCl, 50 mM Tris pH 7.6, 25 mM EDTA and 0.1% SDS (SDS/FW) at 19° C. and radioactivity was then detected by fluorometry. Results indicated that the Bg probes hybridized only with the Bg total nucleic acid demonstrating that the individual piperidone or lactam-based hybridization solutions promoted specific nucleic acid base pairing.

EXAMPLE VI

Specific Detection of Bg Bacterium in Pyrrolidone-Based Hybridization Media

A hybridization media composed of 20% N-cyclohexyl-2-pyrrolidone, and 20% N-hydroxymethyl-2-pyrrolidone, 50 mM Tris, pH 7.6, 25 mM EDTA, and 2% SDS was used to lyse $1 \times 10^8$ cells of Aa, Bi, Ec, Wr, Fn, or Bg in 100 microliter volumes at 19° C. Biotinylated 24-mer oligonucleotide probes complementary to conserved regions of bacterial 16s rRNA (target probes) were added to a final concentration of 100 nanograms per ml. This solution was then incubated with nytran discs which had covalently immobilized 1 microgram of Bg specific oligonucleotide probe (capture probe) for 1 hour at ambient temperature. The solid supports were then washed with SDS/FW at ambient temperature and then incubated with 10 ng/ml of Strepavidin/Horseradish peroxidase (SA/HRP) conjugate in SDS/FW for 30 minutes at ambient temperature. The solid supports were then washed with SDS/FW, FW (filtered water), and then the presence of peroxidase was determined by incubating the filter with a substrate that formed an insoluble product. The results indicated that only the Bg bacterium was detected in the colorimetric sandwich assay. The pyrrolidone hybridization media therefore promoted effective lysis and specific nucleic acid base pairing of the target nucleic acid.

EXAMPLE VII

Extraction of Total Nucleic Acid or DNA

A. Extraction of Total Nucleic Acid or DNA from Bacterial Cells Using GnSCN, Heat and a Lactam To recover total nucleic acid from GnSCN-solubilized bacterial cells approximately $1 \times 10^9$ Bg cells were lysed in 100 microliters of 3M GnSCN, 50 mM Tris pH 7.6, 25 mM EDTA and 2% Sarkosyl. An equivalent of N-methyl-2-pyrrolidone was added (100 microliters)

followed by 500 microliters of phenol and 300 microliters of 1% SDS, 50 mM Tris pH 7.6, 25 mM EDTA and 0.05M NaCl. The solution was heated to 65° C. for 10 minutes and then mixed for 3 minutes at ambient temperature. The solution was then subjected to centrifugation at 10,000 rpm for 5 minutes to force phase separation. The upper aqueous phase was then decanted and nucleic acid was precipitated with 2 volumes of 100% ethanol. Nucleic acid was pelleted for 5 minutes at 10,000 rpm at ambient temperature and the resulting pellet was solubilized with 100 microliters of water. An aliquot was examined by gel electrophoresis. The results indicate that chromosomal DNA and rRNA were efficiently extracted from the GnSCN solubilized bacterial cells.

B. Extraction Of total Nucleic Acid or DNA from Bacterial Cells Using GnSCN and Ethylene Glycol Without the Use of a Heating Step To recover total nucleic acid from GnSCN-solubilized bacterial cells, approximately $1 \times 10^8$ Bg cells were lysed in 100 microliters of 3M GnSCN, 50 mM Tris pH 7.6, 25 mM EDTA and 2% Sarkosyl. 100 microliters of ethylene glycol was then added to the lysate followed by 500 microliters of phenol and 30% microliters of 1% SDS, 50 mM Tris pH 7.6, 25 mM EDTA and 0.05M NaCl. The solution was mixed for 1-3 minutes at ambient temperature. The solution was then subjected to centrifugation at 10,000 rpm for 5 minutes to force phase separation. The upper aqueous phase was then decanted and nucleic acid was precipitated with 2 volumes of 100% ethanol. Nucleic acid was pelleted for 5 minutes at 10,000 rpm at ambient temperature and the resulting pellet was solubilized with 100 microliters of water. An aliquot was examined by gel electrophoresis. The results indicate that chromosomal DNA and rRNA were efficiently extracted from the GnSCN solubilized bacterial cells.

C. Extraction Of total Nucleic Acid or DNA from Bacterial Cells Using GnHCl and a Lactam Without the Use of a Heating Step To recover total nucleic acid from GnHCl-solubilized bacterial cells approximately $1 \times 10^9$ Bg cells were lysed in 100 microliters of 3M GnHCl, 4M urea, 40 mM Tris pH 7.6, 25 mM EDTA and 2% Sarkosyl, 100 microliters of N-methyl-2-pyrrolidone was added to the solution followed by 500 microliters of phenol and 300 microliters of 1% SDS, 50 mM Tris pH 7.6, 25 mM EDTA and 0.05M NaCl. The solution was mixed for 3 minutes at ambient temperature. The solution was then subjected to centrifugation at 10,000 rpm for 5 minutes to force phase separation. The upper aqueous phase was then decanted and nucleic acid was precipitated with 2 volumes of 100% ethanol. Nucleic acid was pelleted for 5 minutes at 10,000 rpm at ambient temperature and the resulting pellet was solubilized with 100 microliters of water. An aliquot was examined by gel electrophoresis. The results indicate that total nucleic acid was efficiently extracted from the GnHCl solubilized bacterial cells.

EXAMPLE VIII

The Sequential Isolation of DNA and rRNA from Bacterial Cell Solubilized with 3M GnSCN To recover DNA and rRNA sequentially from GnSCN-solubilized bacterial cells approximately $1 \times 10^9$ Bg cells were lysed in 100 microliters of 3M GnSCN. 50 mM Tris pH 7.6, 25 mM EDTA and 2% Sarkosyl. An equivalent of N-methyl-2-pyrrolidone was added (100 microliters) followed by 500 microliters of phenol and 300 microliters of 1% SDS, 50 mM Tris pH 7.6, 25 mM EDTA and 0.05M NaCl. The solution was mixed for 3 minutes at ambient temperature and then subjected to centrifugation at 10,000 rpm for 5 minutes to force phase separation. The upper aqueous phase was then decanted and nucleic acid was precipitated with 2 volumes of 100% ethanol. Another 300 microliters of 1% SDS, 50 mM Tris, 25 mM EDTA and 0.05M NaCl was added to the organic (lower phase) and the solution was then heated to 65° C. for 10 minutes and then mixed for 3 minutes at ambient temperature. Again, the nucleic acid in the upper aqueous phase was precipitated by the addition of two volumes of 100% ethanol. Nucleic acid was pelleted for 5 minutes at 10,000 rpm at ambient temperature and the resulting pellet was solubilized with 100 microliters of water. An aliquot was examined by gel electrophoresis. The results indicate that first chromosomal DNA was recovered from the GnSCN lysate followed by the recovery of rRNA. Both nucleic acid types were efficiently extracted and purified from the GnSCN solubilized bacterial cells. This procedure permits the recovery and separation of DNA and rRNA from cells solubilized with chaotropic salts such as GnSCN.

EXAMPLE IX

Recovery of Plasmid DNA from Bacterial Cells Partially Solubilized with Guanidine-HCl Bacterial cells such as *E. coli* can be partially solubilized with weak chaotropic salt solutions such as guanidine-HCl which contain non-ionic detergents. Partially solubilized cells leak RNA and plasmid DNA while retaining chromosomal DNA. These observations were used to develop a method for the rapid and simple isolation of plasmid DNA from *E. coli*.

Approximately $1 \times 10^9$ *E. coli* cells transfected with PBR 322 plasmid were partially solubilized with 100 microliters of 2M guanidine-HCl, 50 mM Tris, 25 mM EDTA and 2% Sarkosyl. The cells were incubated without agitation for 2 minutes at ambient temperature. After the incubation cells and insoluble material was pelleted at 10,000 rpm for 1 minute and the supernatant was decanted and reserved. To the supernatant 100 microliters of N-methyl-2-pyrrolidone was added followed by 500 microliters of phenol and 300 microliters of SDS-extraction buffer.

The solution was mixed for 3 minutes at ambient temperature and the solution was then subjected to centrifugation at 10,000 rpm for 5 minutes to force phase separation. The upper aqueous phase was then decanted and nucleic acid was precipitated with 2 volumes of 100% ethanol. Nucleic acid was pelleted for 5 minutes at 10,000 rpm at ambient temperature and the resulting pellet was solubilized with 100 microliters of water. An aliquot was examined by gel electrophoresis. The results indicate that relative to total extracted nucleic acid, plasmid DNA was preferentially extracted, essentially free of chromosomal DNA, rRNA and protein.

EXAMPLE X

Extraction and Immobilization of Total Nucleic Acid from Bacterial Cells onto Solid Supports for the Detection of Pathogens in Complex Biological Samples using Oligonucleotide Probes To recover total nucleic acid from GnSCN-solubilized bacterial cells a combination of approximately $1 \times 10^8$ Aa, Bg, Bi, Ek, Fn, Wr cells were lysed in 100 microliters of 3M GnSCN, 50 mM Tris pH 7.6, 25 mM EDTA and 2% Sarkosyl. An equivalent of N-methyl-2-pyrrolidone was added (100 microliters) followed by 500 microliters of phenol and 300 microliters of 1% SDS, 50 mM Tris pH 7.6, 25 mM EDTA and 0.05M NaCl. The solution was then heated to 65° C. for 10 minutes and then mixed for 3 minutes at ambient temperature. The solution was then subjected to centrifugation at 10,000 rpm for 5 minutes to force phase separation, 20 microliter portions of the upper aqueous phase were then slotted into Nytran filters using a slotting apparatus.

The filters were then heated to 95° C. for 3 hours. Approximately 50 nanograms of total nucleic acid was immobilized on each nytran slot. $6.5 \times 10^6$ cpm of $^{32}$P-labelled probe (approximately 65 nanograms) of either Aa, Bg, Bi, Ek, Fn, or Wr complementary probe was added to 1 ml of the pyrrolidone-based hybridization solution described above and incubated with nytran filter strips containing Aa, Bg, Bi, Ec, Fn, Wr, and E. coli slots of nucleic acid. Hybridization was allowed to proceed for 3 hours at 19° C. The filters were washed with 0.09M NaCl, 50 mM Tris pH 7.6, 25 mM EDTA and 0.1% SDS (SDS/FW) at ambient temperature and radioactivity was then detected by fluorometry. Results indicated that the specific probes hybridized only with their respective total nucleic acid indicating that target nucleic acid can be directly immobilized onto a solid support after extraction of chaotropic salts containing solubilized nucleic acid with lactam-based solutions.

EXAMPLE XI

The Use of Lactams to Isolate Total Nucleic Acid from Bacterial Cells Without the Use of Phenol A pre-prepared lysis solution composed of 20% N-cyclohexyl-2-pyrrolidone, 20% N-hydroxymethyl-2-pyrrolidone, 10% N-dodecyl-2-pyrrolidione, 50 mM Tris, pH 7.6, 25 mM EDTA, and 2% SDS was used to lyse $1 \times 10^9$ cells of Aa, Bi, Ec, Wr, Fn, Bg, and $1 \times 10^6$ cells of HeLa in 100 microliter volumes. An equal volume of N-methyl-2-pyrrolidone was then added followed by the addition of 200 microliters of N-dodecyl-2-pyrrolidone. The solution immediately became biphasic.

The solution was mixed for 3 minutes at ambient temperature and the solution was then subjected to centrifugation at 10,000 rpm for 5 minutes to force phase separation. The upper aqueous phase was then decanted and nucleic acid was precipitated with 2 volumes of 100% ethanol. Nucleic acid was pelleted for 5 minutes at 10,000 rpm at ambient temperature and the resulting pellet was solubilized with 100 microliters of water. An aliquot was examined by gel electrophoresis. The results indicate that total nucleic acid was preferentially extracted and purified from the cell lysate.

EXAMPLE XII

One Step Assay to Detect Specific Nucleic Acid Sequences of Bacterial Pathogens

A pre-prepared lysis solution composed of 20% N-cyclohexyl-2-pyrrolidone, 20% N-hydroxymethyl-2-pyrrolidone, 10% N-dodecyl-2-pyrrolidone, 50 mM Tris, pH 7.6, 25 mM EDTA, and 2% SDS and containing 1 to 5 mg of 5 micron beads (silica, (Spherisorb) from Phase Sep. Deeside Ind., Queensferry, Clwyd, U.K.) onto which 1 to 2 micrograms of Bg specific oligonucleotide probe has been covalently immobilized, and which also contained $1 \times 10^6$ cpm of $^{32}$P oligonucleotide probe (specific activity of $1 \times 10^7$ cpm per microgram) complementary to Bg specific regions of the 16s rRNA was used to lyse $1 \times 10^6$ cells of Aa, Bi, Ec, Wr, Fn, and Bg in 100 microliter volumes at 19° C. The solution was then incubated for 30 minutes at room temperature. The solid supports were then washed with SDS/FW at ambient temperature to remove un-hybridized material and radioactive probes. The solid supports were then monitored for radioactivity by scintillation counting. The results indicated that only Bg cells were detected when using Bg specific oligonucleotide signal probes and not when using specific labelled probes for Aa, Bi, Ek, Fn or Wr. Thus, in 30 minutes $1 \times 10^6$ Bg cells were detected in a simple one step hybridization assay.

We claim:

1. A method for isolating nucleic acid from a sample containing a complex biological mixture of nucleic acids and non-nucleic acids, comprising:
combining the sample with an extraction solution comprising at least one monomeric lactam at a concentration of about 5% to about 70% of the total volume of the extraction solution, wherein the lactam is capable of forming a biphasic solution after combination with the sample; and
isolating nucleic acid from the resulting combined solution.

2. The method of claim 1, wherein the lactam is selected from the group of compounds having the formula:

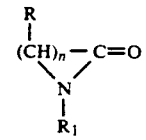

wherein n=3 to 8 (with the total number of R substituents being 3 to 8), and $R_1$ is selected from the group consisting of:
hydrogen,
alkyl of 1 to 20 carbons,
aryl of 6 to 10 carbons,
arylalkyl of 7 to 20 carbons,
alkylcarboxyamide of 1 to 20 carbons,
hydroxyarylalkyl of 7 to 20 carbons,
N-mono-substituted alkylcarboxyamide,
N,N-dialkyl-substituted alkylcarboxyamide,
alkylcarboxylate of 2 to 20 carbons,
acyl of 2 to 20 carbons,
cycloalkane of 4 to 10 carbons,
hydroxyalkyl,
and cyanoalkyl;

and where the R substituents can be the same or different and selected from a group consisting of hydrogen, halogen and alkyl of 1 to 5 carbons such that the total carbon number for all R substituents does not exceed 20; with the further provision that the total carbon number of the $R_1$ substituent does not exceed 20 and where at least one R designated substituent must be hydrogen.

3. The method of claim 2, wherein n = 3 to 6.

4. The method of claim 2, wherein at least one R substituent is methyl.

5. The method of claim 2, wherein the $R_1$ substituent and all of the R substituents are hydrogen.

6. The method of claim 2, wherein the $R_1$ substituent is other than hydrogen and all of the R substituents are hydrogen.

7. The method of claim 2, wherein the $R_1$ substituent is a cycloalkane of 4 to 7 carbons.

8. The method of claim 2, wherein the $R_1$ substituent is $-CH_2-CH_2OH$.

9. The method of claim 2, wherein the $R_1$ substituent is hydroxyarylalkyl.

10. The method of claim 2, wherein the $R_1$ substituent is dodecyl.

11. The method of claim 2, wherein the $R_1$ substituent is methyl.

12. The method of claim 1, wherein the lactam is a compound selected from the group consisting of 2-pyrrolidone, N-ethyl-2-pyrrolidone, N-cyclohexyl-2pyrrolidone, N-dodecyl-2-pyrrolidone, N-methyl-2-pyrrolidone, N-hydroxyethyl-2-pyrrolidone, N-methyl-2-piperidone, 2-ε-caprolactam, N-methyl-2-caprolactam, 2-piperidone and N-(4-hydroxybenzyl)pyrrolidone.

13. The method of claim 1, wherein the nucleic acid is plasmid DNA.

14. The method of claim 1, wherein the resulting combined solution is further mixed and allowed to become biphasic before the nucleic acid material is isolated.

15. The method of claim 14, wherein the nucleic acid material is isolated by precipitation with ethanol from an aqueous phase.

16. The method of claim 1, wherein the resulting combined solution further comprises a chaotropic agent.

17. The method of claim 1, wherein the sample is also combined with a solution comprising GnHCl.

18. A composition for the extraction of nucleic acid comprising:
a buffer solution; and
at least one monomeric lactam at a concentration of about 5% to about 70% of the total volume of the buffer solution.

19. A nucleic acid extraction kit comprising, in one or more containers:
a buffer solution; and
at least one monomeric lactam at a concentration of about 5% to about 70% of the total volume of the buffer solution.

* * * * *